US012478789B2

(12) United States Patent
Schuster et al.

(10) Patent No.: US 12,478,789 B2
(45) Date of Patent: Nov. 25, 2025

(54) LEAD CONNECTOR WITH ASSEMBLY FRAME AND METHOD OF MANUFACTURE

(71) Applicant: Heraeus Medical Components LLC, St. Paul, MN (US)

(72) Inventors: Paul Schuster, St. Paul, MN (US); Jonathan West, St. Paul, MN (US); Benjamin Locke, St. Paul, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 606 days.

(21) Appl. No.: 17/443,571

(22) Filed: Jul. 27, 2021

(65) Prior Publication Data

US 2022/0023644 A1 Jan. 27, 2022

Related U.S. Application Data

(60) Provisional application No. 63/057,033, filed on Jul. 27, 2020.

(51) Int. Cl.
*A61N 1/375* (2006.01)
*H01R 13/50* (2006.01)
(Continued)

(52) U.S. Cl.
CPC ........... *A61N 1/3752* (2013.01); *H01R 13/50* (2013.01); *H01R 43/16* (2013.01); *H01R 43/24* (2013.01); *H01R 2201/12* (2013.01)

(58) Field of Classification Search
CPC ........ A61N 1/3752; A61N 1/05; A61N 1/056; A61N 1/3754; A61N 1/3956; A61N 1/37512; A61N 1/372; A61B 5/0031; A61B 2562/222; A61B 2017/00526; H01R 13/5224; H01R 2201/12; H01R 31/06; H01R 43/20; H01R 13/111; H01R 43/00;
(Continued)

(56) References Cited

U.S. PATENT DOCUMENTS 6,249,708 B1 * 6/2001 Nelson .................. A61N 1/056 607/122
6,817,905 B2 11/2004 Zart et al.
(Continued)

FOREIGN PATENT DOCUMENTS

WO 01/99239 12/2001

*Primary Examiner* — Benjamin J Klein
*Assistant Examiner* — Daniel Tehrani
(74) *Attorney, Agent, or Firm* — Dicke, Billig & Czaja, PLLC

(57) ABSTRACT

One aspect is a method of manufacturing a lead connector for an implantable medical device. The method includes connecting proximal ends of a plurality of conductive pins to a corresponding one of a plurality of ring contacts to form a plurality of ring-pin subassemblies, assembling each of the plurality of ring-pin subassemblies on an assembly frame, including inserting the plurality of conductive pins in a corresponding plurality of openings within the assembly frame such that the corresponding plurality of ring contacts are spaced along a longitudinal dimension of the assembly frame, arranging the assembly frame along with the conductive pins and corresponding ring contacts within a mold cavity, filling the mold cavity with a mold material that surrounds the assembly frame, and removing a resulting lead connector from the mold cavity.

9 Claims, 11 Drawing Sheets

(51) Int. Cl.
*H01R 43/16* (2006.01)
*H01R 43/24* (2006.01)

(58) Field of Classification Search
CPC ........ H01R 13/20; H01R 13/50; H01R 43/16; H01R 43/24; H01R 13/405; H01R 24/58
See application file for complete search history.

(56) References Cited

U.S. PATENT DOCUMENTS

| | | | |
|---|---|---|---|
| 7,083,474 | B1 | 8/2006 | Fleck et al. |
| 7,167,749 | B2 | 1/2007 | Biggs et al. |
| 7,175,478 | B2 | 2/2007 | Ollivier |
| 7,241,180 | B1 | 7/2007 | Rentas Torres |
| 7,489,968 | B1 | 2/2009 | Alexander |
| 7,601,033 | B2 | 10/2009 | Ries et al. |
| 7,983,754 | B2 | 7/2011 | Kessler et al. |
| 8,382,529 | B2 | 2/2013 | Lim et al. |
| 8,628,348 | B2 | 1/2014 | Ries et al. |
| 8,641,436 | B2 | 2/2014 | Regnier et al. |
| 8,673,194 | B2 | 3/2014 | Lee et al. |
| 8,761,887 | B2 | 6/2014 | Schramm et al. |
| 8,914,110 | B2 | 12/2014 | He et al. |
| 9,072,909 | B1 | 7/2015 | Hughes |
| 9,101,776 | B2 | 8/2015 | Hughes |
| 9,209,544 | B2 | 12/2015 | Glynn et al. |
| 9,742,130 | B2 | 8/2017 | Glynn et al. |
| 2008/0303728 | A1 | 12/2008 | Lee et al. |
| 2010/0210146 | A1 | 8/2010 | Jang et al. |
| 2012/0151765 | A1 | 6/2012 | James, IV et al. |
| 2014/0107751 | A1 | 4/2014 | Regnier et al. |
| 2014/0213118 | A1 | 7/2014 | Glynn et al. |
| 2014/0309719 | A1 | 10/2014 | Oster et al. |
| 2015/0165217 | A1 | 6/2015 | Hughes |

* cited by examiner

LEAD CONNECTOR WITH ASSEMBLY FRAME AND METHOD OF MANUFACTURE

CROSS-REFERENCE TO RELATED APPLICATION

This Non-Provisional Patent application claims the benefit of the filing date of U.S. Provisional Patent Application Ser. No. 63/057,033, filed Jul. 27, 2020, ENTITLED “LEAD CONNECTOR WITH ASSEMBLY FRAME AND METHOD OF MANUFACTURE,” which is incorporated herein by reference.

TECHNICAL FIELD

An implantable medical lead typically includes a tubular-shaped main lead having one or more conductors or coils to sense or provide stimulative biologic, electrical signals, and a lead connector coupled to one end of the main lead. In one embodiment, the lead connector is, in-turn, configured to electrically and mechanically plug into and couple to a header or connector bore of a pacemaker, implantable cardioverter defibrillator (“ICD”), or other type of pulse generator.

BACKGROUND

One type of implantable medical lead includes an IS4/DF4 lead connector, which is a standardized lead connector having an injection molded, reaction injection molded (RIM) or potted, cylindrical body (typically of a thermoplastic, or thermoset material). The connector body has a proximal end configured to connect into a header of an active implantable device of some type, and a distal end configured to connect to the conductors/coils within the main lead. Such lead connectors have multiple electrical contacts in the form of contact rings which are spaced along and are flush with a surface of the connector body. Lead connectors may also include a pin contact extending from the proximal end. A conductor typically extends through the lead body from each contact ring and projects from the distal end of the molded body so as to provide a connection point for the conductors of the main lead. Similarly, a main body pin may extend along a central axis of the lead connector from the pin contact at the proximal end and also project from the distal end of the molded body.

Conventional practices for the manufacture of lead connectors include an injection molding process, or a reaction injection molding process, or liquid silicone molding process, or a potting process wherein the ring connectors, conductive pins, and the central pin/pin contact (if being employed) are arranged within a mold cavity. A thermoplastic material, or other suitable material, is then injected into the mold cavity to over-mold the conductive pins, ring connectors, and main body pin to form the cylindrical body of the lead connector.

Tight tolerances are required for the safe and effective performance of lead connectors, including IS4/DF4 connectors. However, the injection molding process presents many challenges and shortcomings that make maintenance of such tight tolerance difficult to meet and which can result in high production costs and low manufacturing yields. For these and other reasons, there is a need for the present embodiments.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

Figure 1:
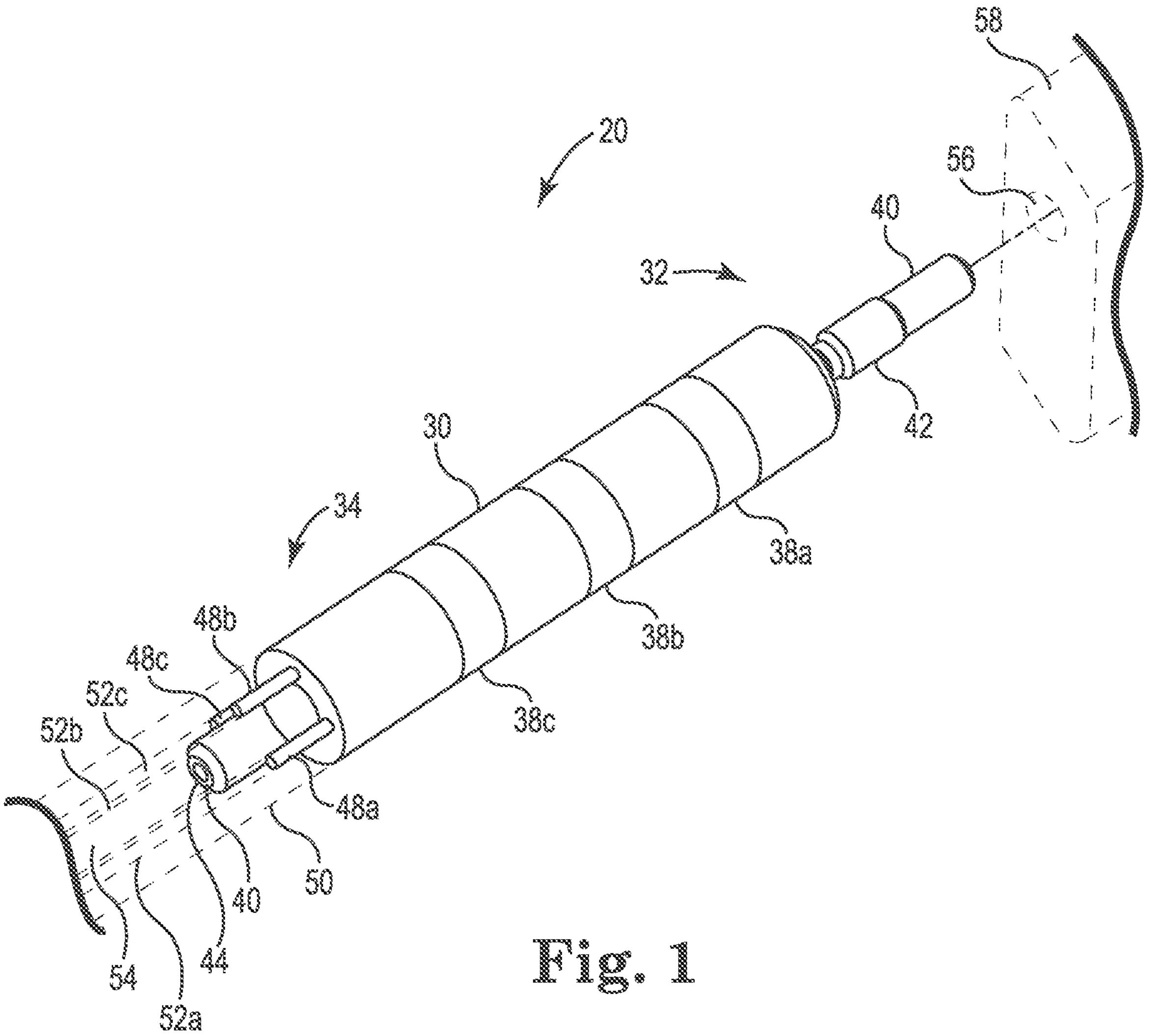
FIG. 1 illustrates a perspective view of a lead connector according to one embodiment.
Figure 2:
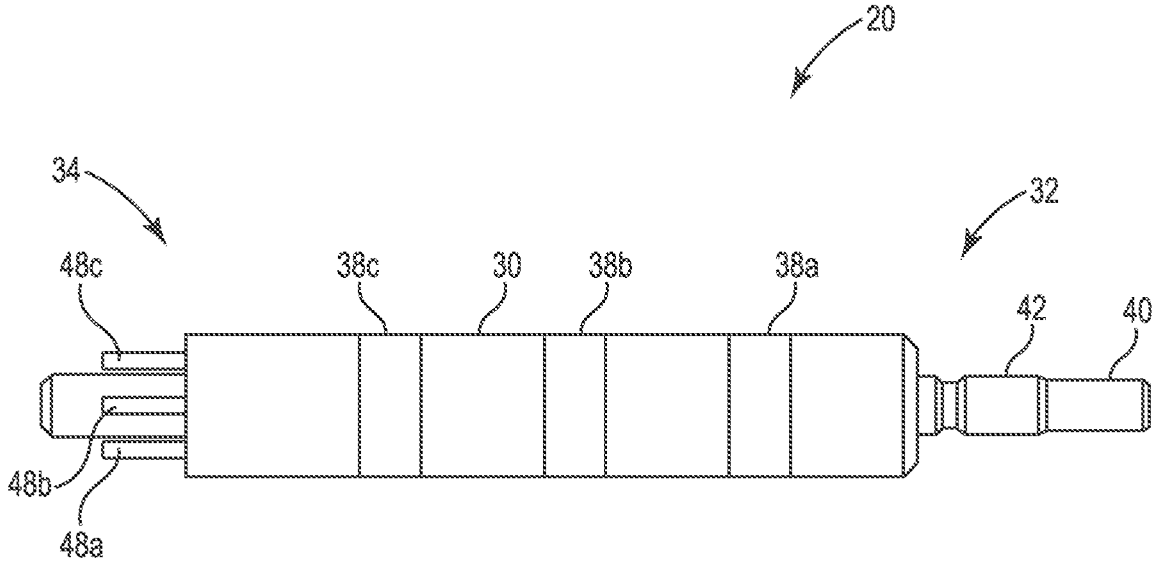
FIG. 2 illustrates a side view of the lead connector depicted in FIG. 1, according to one embodiment.

FIG. 1 is a perspective view, and FIG. 2 is a side view of an example of a lead connector 20 for an implantable medical device. Lead connector 20 can be any of a variety of implantable leads, including, for example, an IS4/DF4 lead connector. Lead connector 20 includes a cylindrical body 30 having a proximal end 32 and a distal end 34 according to one embodiment.

In one embodiment, lead connector 20 includes first-third ring contacts 38*a*, 38*b*, 38*c*, disposed in a spaced-apart fashion along a longitudinal dimension of body 30, and a central pin 40 axially extending from proximal end 32 having a pin contact 42. First-third ring contacts 38*a*-38*c* are imbedded in and have a same outer diameter as body 30 so as to provide cylindrical body 30 with a uniform circumferential surface. Body 30 may be formed of an electrically non-conductive polymer material (e.g. polyurethane, polyetheretherketone (PEEK), polysulfone, etc.), epoxy, liquid silicone rubber, or any other suitable type of electrically non-conductive material.

In one embodiment, first-third conductive pins 48*a*, 48*b*, and 48*c* axially extend through body 30 respectively from first-third ring contacts 38*a*, 38*b* and 38*c*, and project from distal end 34 of body 30. In one embodiment, first-third conductive pins 48*a*-48*c* are generally rigid wires that form first-third conductive pins 48*a*-48*c*. Similarly, central pin 40 extends axially through body 30 and projects from distal end 34, with central pin 40 defining a central lumen 44. In other embodiments, central pin 40 may extend axially through body 30, but project from distal end 34 on the outer periphery, such as with first-third conductive pins 48*a*-48*c*.

In one embodiment, lead connector 20 is configured to be coupled to a flexible implantable lead. For example, lead connector 20 can be coupled at its distal end 34 to a flexible implantable lead 50 (illustrated in dashed lines in FIG. 1). In one embodiment, first-third conductive pins 48*a*-48*c* serve as a contact point to which conductors 52*a*, 52*b*, and 52*c* of flexible implantable lead 50 are electrically and mechanically connected, such as by laser welding, for example, to thereby place lead conductors 52*a*-52*c* in electrical communication with first-third ring contacts 38*a*-38*c*. Lead 50 may also include a central conductor 54 which is in electrical communication with pin contact 42 via central lumen 44. In one embodiment, conductors 52*a*-52*c* and central conductor 54 extend through lead 50 to corresponding coil or sensor.

In one embodiment, lead connector 20 is configured at its proximal end 32 to be coupled to a device. For example, in one embodiment, lead connector 20 is configured to be inserted into a receptacle or bore of 56 of header of a pulse generator 58 (illustrated in dashed lines in FIG. 1) of some type, such as a pacemaker or implantable cardioverter defibrillator ("ICD"), for example. Complementary contacts within pulse generator contact ring contacts 38*a*-38*c* and pin contact 42, thereby placing pulse generator 58 in electrical communication with sensors and/or coils associated with lead 50.

It is noted that while lead connector 20 has been described with an example primarily in the context of an IS4/DF4 lead connector, one skilled in the art understands that the use of an assembly frame described below, as well as manufacturing techniques described herein, are applicable to other types of lead connectors as well. Accordingly, the features of lead connector 20, including as assembly frame, and methods of manufacture described, herein should not be interpreted as being limited to only IS4/DF4 lead connectors.

Figure 3:
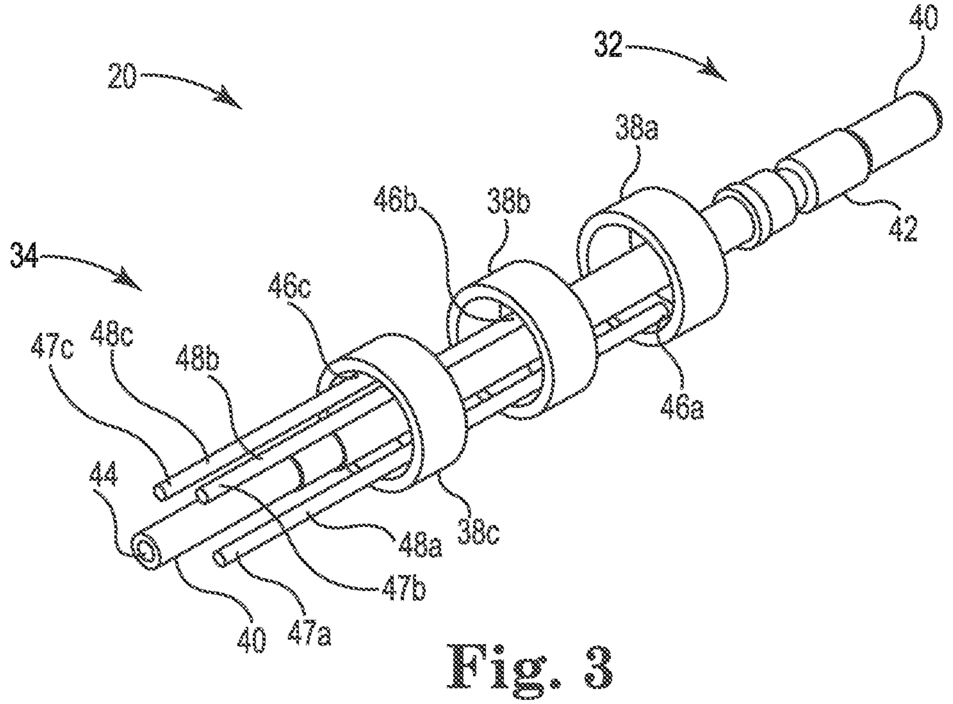
FIG. 3 illustrates a perspective view illustrating portions of a lead connector in a stage of assembly prior to over-molding, according to one embodiment.
Figure 4:
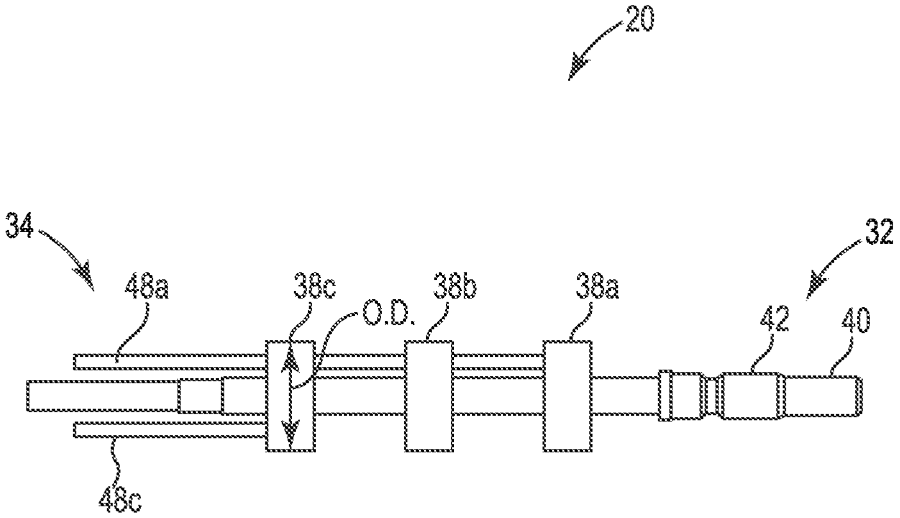
FIG. 4 illustrates a side view of illustrating portion of the lead connector depicted in FIG. 3, according to one embodiment.
Figure 5:
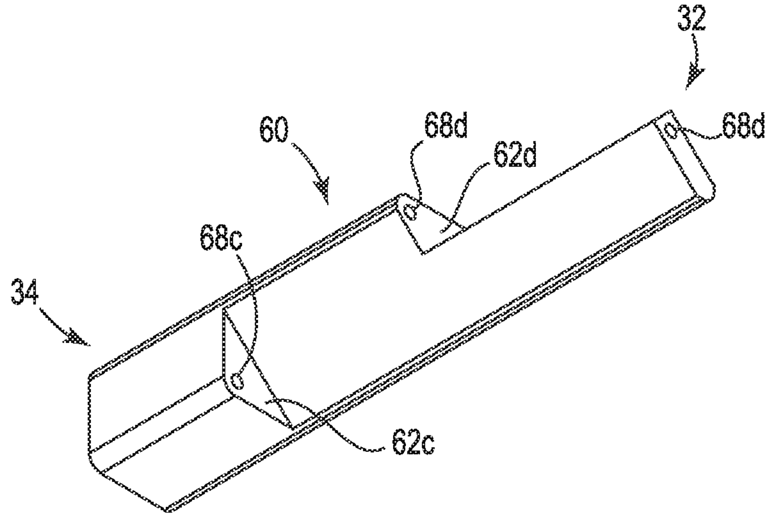
FIGS. 5-7 illustrate perspective views of an assembly frame, according to one embodiment.
Figure 6:
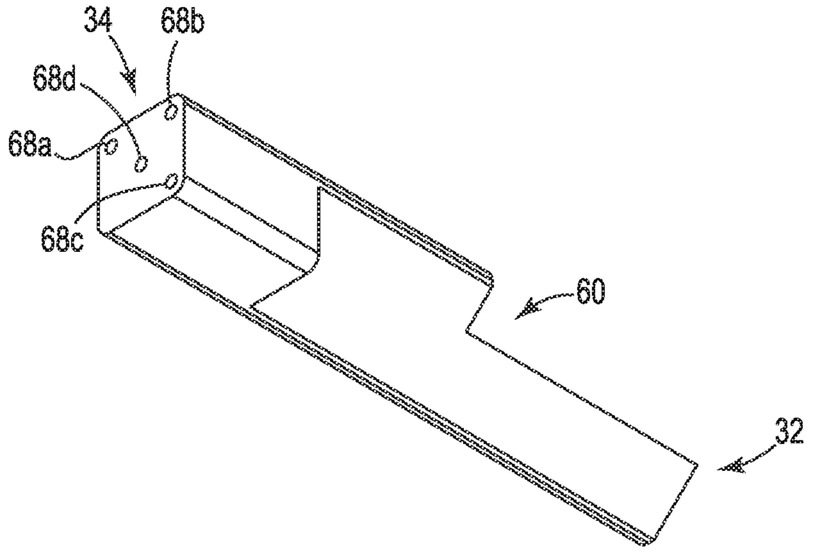

FIGS. 3 and 4 are respective perspective and side views illustrating portions of lead connector 20, prior to being over-molded to form body 30, according to one embodiment. As illustrated, prior to the molding process for forming body 30, first-third conductive pins 48*a*, 48*b*, and 48*c* are respectively connected to an inner surface of corresponding first-third ring contact 38*a*, 38*b*, 38*c*, such as by laser welding, or soldering, for example, to form first-third ring-pin subassemblies 38*a*/48*a*, 38*b*/48*b*, 38*c*/48*c*.

In one embodiment, each of first-third conductive pins 48*a*, 48*b*, and 48*c* respectively have proximal ends 46*a*, 46*b*, and 46*c* and distal ends 47*a*, 47*b*, and 47*b*. In one embodiment, the proximal ends 46*a*, 46*b*, and 46*c* are respectively fixed to ring contacts 38*a*, 38*b*, 38*c*, while the distal ends 47*a*, 47*b*, and 47*b* each extend back toward the distal end 34 of lead connector 20.

In one embodiment, first-third ring-pin subassemblies 38*a*/48*a*, 38*b*/48*b*, 38*c*/48*c* are configured for "nesting", such that first conductive pin 48*a* extends from its proximal end 46*a* at first ring 38*a* back through second and third rings 38*b* and 38*c* toward the distal end 34 of lead connector 20. Similarly, second conductive pin 48*b* extends from its proximal end 46*b* at second ring 38*b* back through third ring 38*c* toward the distal end 34 of lead connector 20. Third conductive pin 48*c* extends from its proximal end 46*c* at third ring 38*c* back toward the distal end 34 of lead connector 20.

In one embodiment, central pin 40 is also arranged so as to extend through all three ring contacts 38*a*-38*c* from proximal end 32 to distal end 34.

In one embodiment, it is important that conductive pins extending through rings to which they are not coupled do not inadvertently make contact with these rings. For example, while first conductive pin 48*a* is coupled to first ring 38*a*, it cannot make contact with second and third rings 38*b* and 38*c* as it extends toward the distal end 34 of lead connector 20. Touching another ring can cause an electrical short. Even getting too near a ring can leave the device susceptibility to electrical arcing.

In some designs, an insulative coating is added to each conductive pin or wire and it extends through adjacent rings in order to avoid inadvertant electrical contact with rings. Similarly, an insulating sleeve can be added to each wire or pin. Both processes, however, add complexity and cost to the manufacturing of a lead connector. For example, a coated wire must be ablated on each of the proximal and distal ends to provide electrical conductivity where it is needed (at connection points). Furthermore, adding individual insulating tubing to each wire is time consuming and adds multiple parts. All of this adds to manufacturing time and cost.

FIGS. 5-8 illustrate various perspective views and an end view of assembly frame 60 of lead connector 20 in accordance with one embodiment. In one embodiment, assembly frame 60 includes first-third steps 62*a*, 62*b* and 62*c*. In one embodiment, assembly frame 60 includes first-fourth openings 68*a*, 68*b*, 68*c*, and 68*d*, each extending the length of the assembly frame 60. In one embodiment, first-fourth openings 68*a*, 68*b*, 68*c*, and 68*d*, are configured as cylindrical lumens with a diameter that accommodates conductive pins 48*a*, 48*b*, and 48*c*. Proximal end 32 and distal end 34 of assembly frame 60 correlate with that of lead connector 20. In one embodiment, assembly frame 60 assists in the assembly of lead connector 20 and overcomes many of the disadvantages of prior systems.

Figure 9:
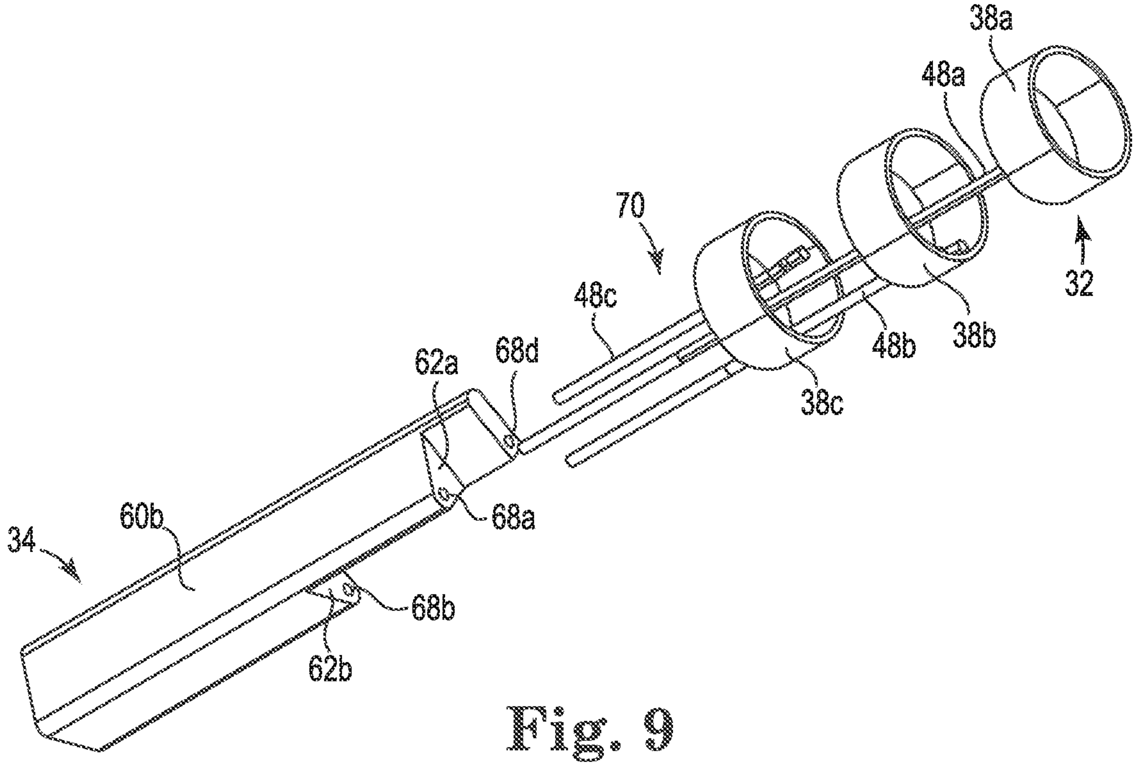
FIG. 9 illustrates an exploded view of a ring-pin assembly, according to one embodiment.

In one embodiment, during the assembly of lead connector 20, each first-third ring-pin subassemblies 38*a*/48*a*, 38*b*/48*b*, 38*c*/48*c* are individually assembled onto assembly frame 60 to form a ring-pin assembly 70. FIG. 9 illustrates an exploded view of a partially assembled ring-pin assembly 70 for forming lead connector 20, where each of first-third ring-pin subassemblies 38*a*/48*a*, 38*b*/48*b*, 38*c*/48*c* are adjacent assembly frame 60.

Figure 7:
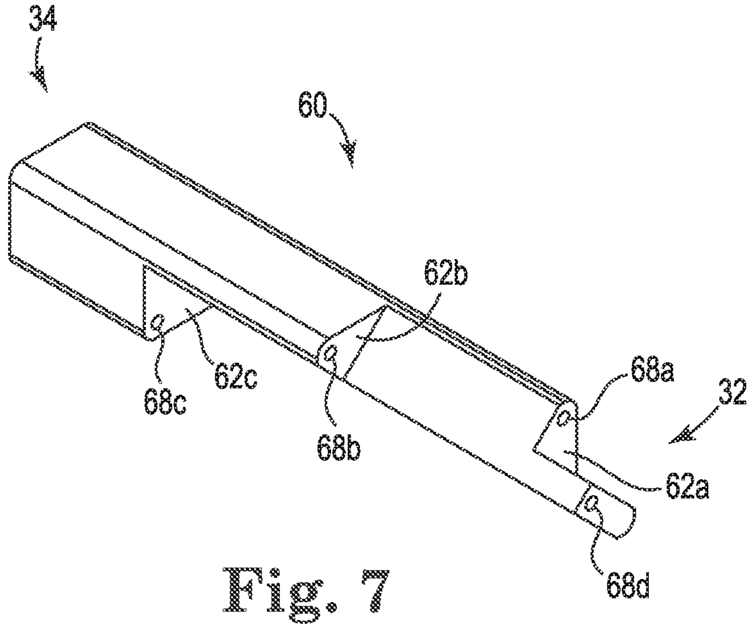

In one embodiment, third ring-pin subassembly 38*c*/48*c* is placed over assembly frame 60 by sliding third conductive pin 48*c* into third opening 68*c* (not visible in FIG. 9, but illustrated in FIGS. 7-8) and sliding third ring 38*c* over assembly frame 60 until it engages third step 62*c* (not visible in FIG. 9, but illustrated in FIG. 7). Next, second ring-pin subassembly 38*b*/48*b* is placed over assembly frame 60 by sliding second conductive pin 48*b* into second opening 68*b* and sliding second ring 38*b* over assembly frame 60 until it engages second step 62*b*. Finally, first ring-pin subassembly 38*a*/48*a* is placed over assembly frame 60 by sliding first conductive pin 48*a* into first opening 68*a* and sliding first ring 38*a* over assembly frame 60 until it engages first step 62*a*. In one embodiment, central pin 40 is inserted through fourth opening 68*d* so that it extends out of assembly frame 60 on both proximal end 32 and distal end 34. Fully assembled ring-pin assembly 70 is illustrated in FIG. 10.

In one embodiment, assembly frame 60 is configured with first-third steps 62*a*, 62*b* and 62*c* being spaced along its longitudinal dimension such that when a respective ring 38*a*-48*c* is placed adjacent the step, the ring will be situated in a desired longitudinal location relative to the final lead connector 20. The longitudinal spaces between steps can be adjusted and tailored to any particular application or standard to ensure proper spacing between rings. Similarly, first-fourth openings 68*a*, 68*b*, 68*c*, and 68*d* are configured to ensure that respective conductive pins 48*a*, 48*b*, 48*c*, and 48*d* are located properly to ensure conductive contact with appropriate rings and avoid inadvertent contact with the other rings and other conductors.

Figure 8:
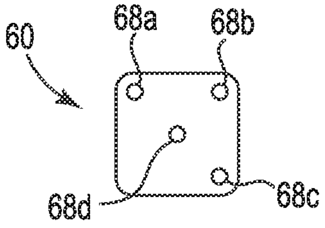
FIG. 8 illustrates an end view of an assembly frame, according to one embodiment.

In one embodiment, first-third openings 68*a*, 68*b*, 68*c*, and thus, first-third conductive pins 48*a*, 48*b*, 48*c*, are arranged generally on the outer perimeter of assembly frame 60, such as viewed from the end illustrated in FIG. 8. In one embodiment, conductive pins 48*a*, 48*b*, 48*c* are spaced apart around the perimeter to ensure no one conductor is too close to another, or too close to a ring to which it is not coupled.

Figure 10:
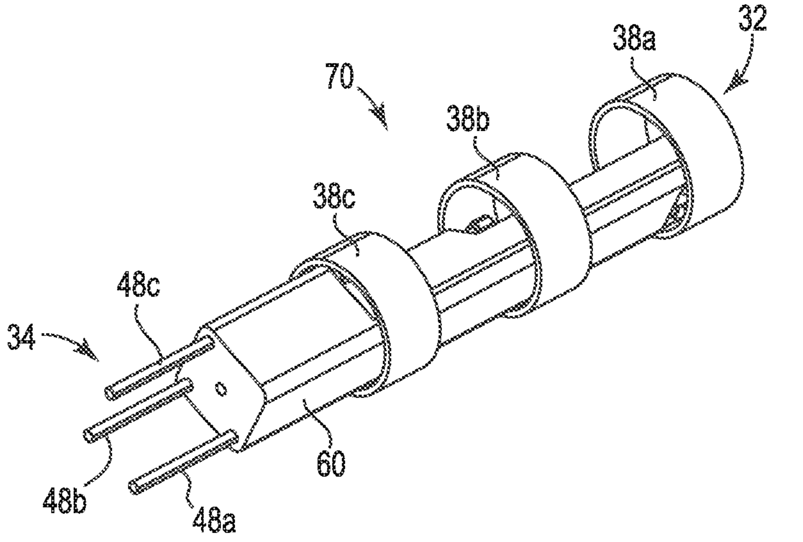
FIG. 10 illustrates a perspective view of a ring-pin assembly, according to one embodiment.

In one embodiment, once first-third ring-pin subassemblies 38*a*/48*a*, 38*b*/48*b*, 38*c*/48*c* are individually placed on to assembly frame 60, the combined ring-pin assembly 70, illustrated in FIG. 10, is then placed into a mold for over-molding to produce a completed lead connector 20, such as illustrated by FIGS. 1 and 2. Generally, the conductive pins and central pin/pin contact are positioned within the mold cavity with their ends extending through corresponding exit holes formed in the mold tool steel. A thermoplastic material, or other suitable material, is then injected under pressure into the cavity to over-mold the subassemblies and main contact pin to form the cylindrical body of the lead connector.

Figure 11:
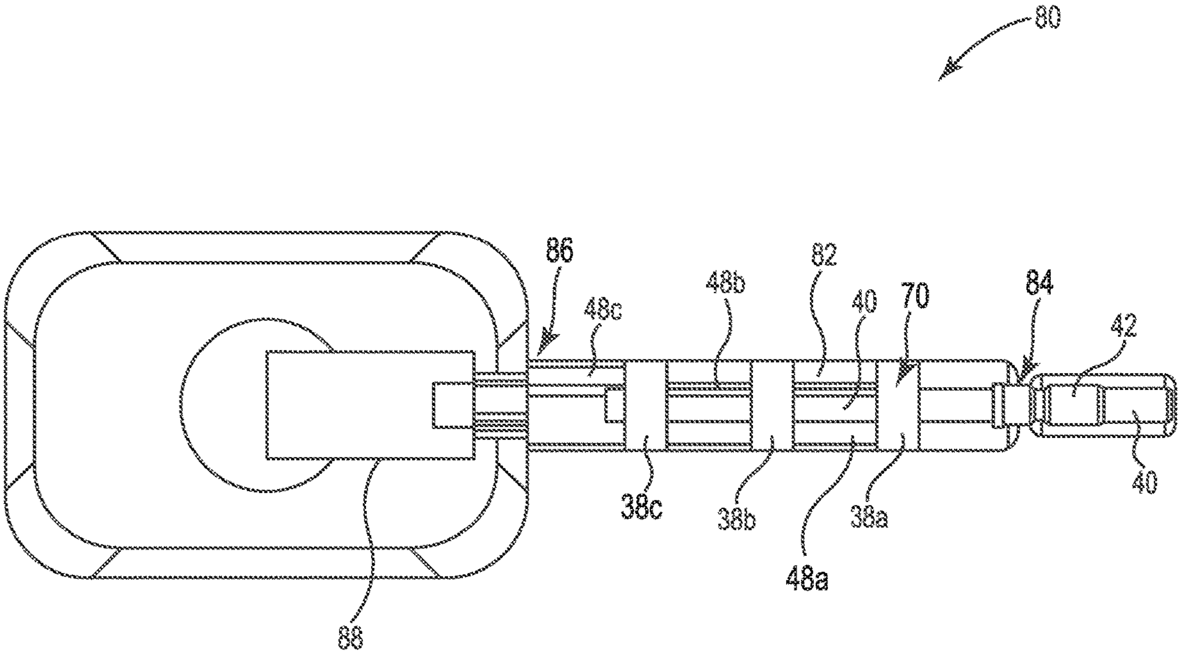
FIG. 11 illustrates a ring-pin assembly in a mold cavity, according to one embodiment.

FIG. 11 generally illustrates ring-pin assembly 70 placed in an injection molding system 80 for over-molding to form body 30, and thereby form completed lead connector 20. Molding system 80 includes a mold cavity 82 configured to receive a ring-pin assembly 70. According to one embodiment, mold cavity 82 is substantially tubular or cylindrical in shape, and has an inside diameter equal to that of the outside diameter of body 30 of lead connector 20. Mold cavity 82 includes an opening 84 at one end through which the proximal end of central pin 40, including pin contact 42, extends. Mold cavity 86 includes an opening 86 at an opposing end through which portions of the distal end of ring-pin assembly 70 extend, including the portions of conductive pins 38*a*-38*c* and central pin 40. Mold system 80 can also include a block 88 configured to retain a portion for connecting to pins 38*a*-38*c*.

In one embodiment, assembly frame 60 obviates the need for an assembly operator to carefully load each ring-pin subassembly into the mold cavity 82 and to carefully position them to ensure proper spacing and alignment. Traditional manufacturing process requires that each ring-pin subassembly must be nested and inserted individually into the mold tool, such that each ring and each conductor is precisely located to ensure proper spacing, thereby requiring skill and extra time during the assembly process.

After ring-pin assembly 70 is loaded into mold cavity 82, mold material is injected into mold cavity 82 to over-mold those portions of ring-pin assembly 70 within mold cavity 82 and form connector body 30. After removal from the mold cavity, assembly frame 60 is integral with body 30 and forms a portion of the finished lead connector 20. The resulting finished lead connector 20 (as illustrated by FIGS. 1 and 2) is then removed from mold system 80.

In one embodiment, assembly frame 60 is made of a material that is the same as the mold material injected into mold cavity 82. Since the mold material flows in hot, some or all portions of assembly frame 60 may melt and mix with the injected mold material. In other embodiments, assembly frame 60 is made of a material that is the different than the mold material injected into mold cavity 82. For example the materials may have different durometers and/or meting points, such that in some circumstances, the material of assembly frame 60 will remain relatively intact, but fully surrounded by the molding material in the final lead connector 20.

In one embodiment, the rigid structure of assembly frame 60, combined with a secure fit of first-third conductive pins 48*a*, 48*b*, 48*c* with first-third openings 68*a*, 68*b*, 68*c*, prevents the forces of mold material injected into the mold cavity 82 from moving and misaligning conductive pins 48*a*, 48*b*, 48*c* and rings 38*a*, 38*b*, 38*c*. In traditional manufacturing process, the ring-pin subassemblies are free-standing during molding. High injection pressure used in the injection molding process can cause the conductive pins and central pin to move within the mold cavity, thereby causing the electrical characteristics to potentially vary between lead connectors, and even causing shorting issues should the conductive pins be moved into contact with one another or other conductive elements within the lead connector. Forces created inside the mold cavity subject the pins to potential movement and bowing (forcing curvature) during the molding process. For example, during traditional manufacturing process, there are opportunities for electrical shorts or arcing between conductor paths. During the nesting process and the molding process it is imperative that the pin from one ring does not touch or come too near another ring or pin. Assembly frame 60 ensures such faults are avoided.

Figure 12:
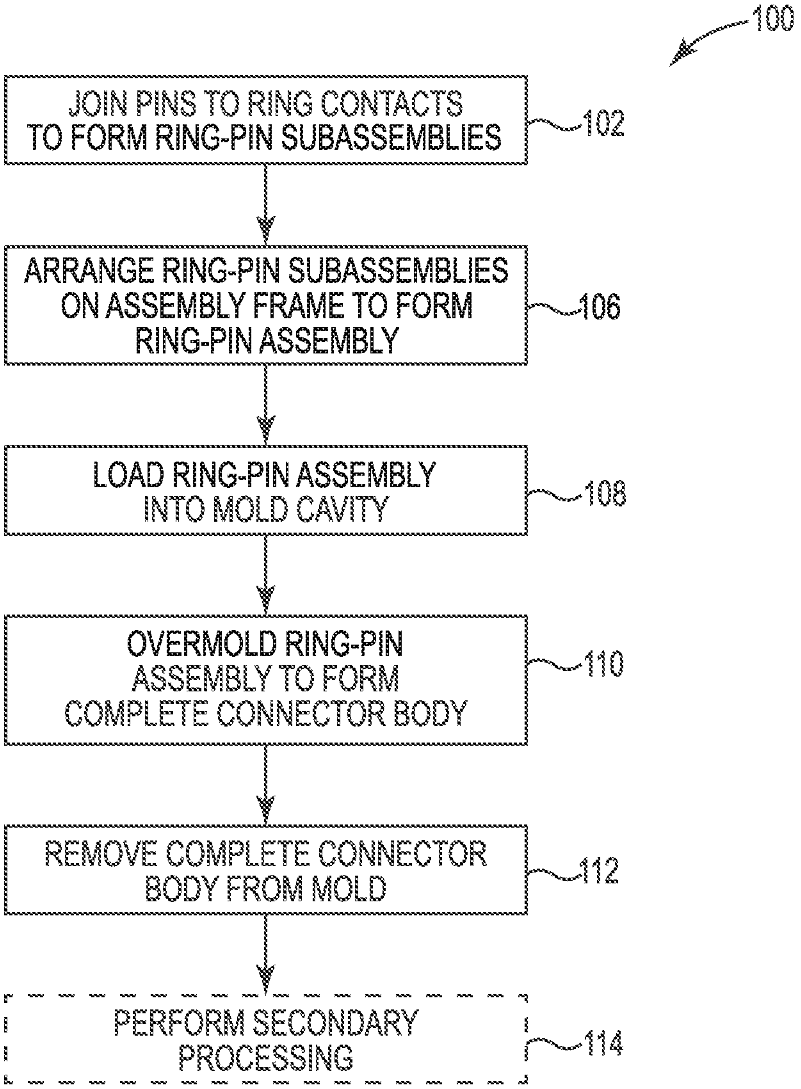
FIG. 12 illustrates a method of forming a lead connector, according to one embodiment.

FIG. 12 is flow diagram illustrating a process 100 for forming a lead connector, such as lead connector 20, according to one embodiment. Process 100 begins at 102 where conductive pins, such as conductive pins 48*a*-48*c* are joined (e.g. by laser welding) to ring contacts, such as ring contacts 38*a*-38*c*, to form ring-pin sub-assemblies.

At 106, the ring-pin sub-assemblies are arranged onto the assembly frame to form a ring-pin assembly. For example, according to one embodiment as illustrated by FIG. 9, third ring-pin subassembly 38*c*/48*c* is arranged over assembly frame 60 by sliding third conductive pin 48*c* into third opening 68*c* and sliding third ring 38*c* over assembly frame 60 until it engages third step 62*c*, second ring-pin subassembly 38*b*/48*b* is arranged over assembly frame 60 by sliding second conductive pin 48*b* into second opening 68*b* and sliding second ring 38*b* over assembly frame 60 until it engages second step 62*b*, and first ring-pin subassembly 38*a*/48*a* is arranged over assembly frame 60 by sliding first conductive pin 48*a* into first opening 68*a* and sliding first ring 38*a* over assembly frame 60 until it engages first step 62*a*.

At 108, the ring-pin assembly, such as ring-pin assembly 70, is loaded into a mold cavity of an injection molding system, such as mold cavity 82 of molding system 80 (see FIG. 11). Mold material is injected into the mold cavity to over-mold the portions of ring-pin assembly 70 within the mold cavity 82.

At 112, the finished lead connector, such as lead connector 20, is removed from the mold. At 114, if required, post mold secondary processing is performed, such as annealing, plasma treatment, machining, trimming or cleaning. For example, some thermoplastics require annealing in order to meet dimensional specification. Machining can be done to add a feature on an inner diameter or outer diameter of the lead connector that cannot be effectively formed via injection molding.

Figure 13A:
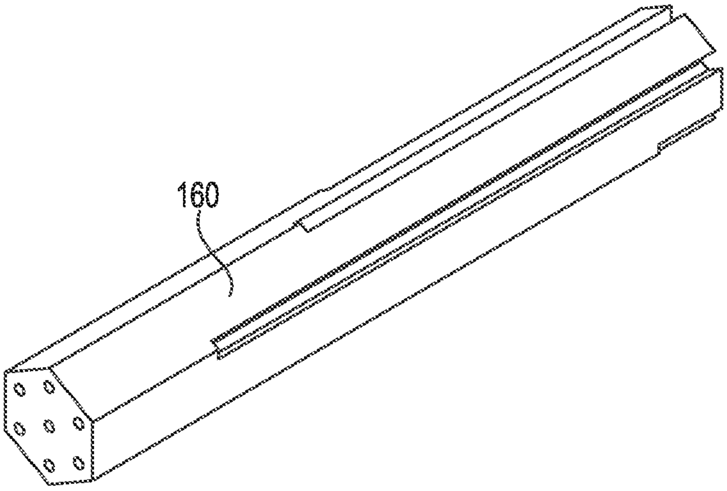
FIGS. 13A and 13B illustrate perspective views of an assembly frame, according to one embodiment.
Figure 13B:
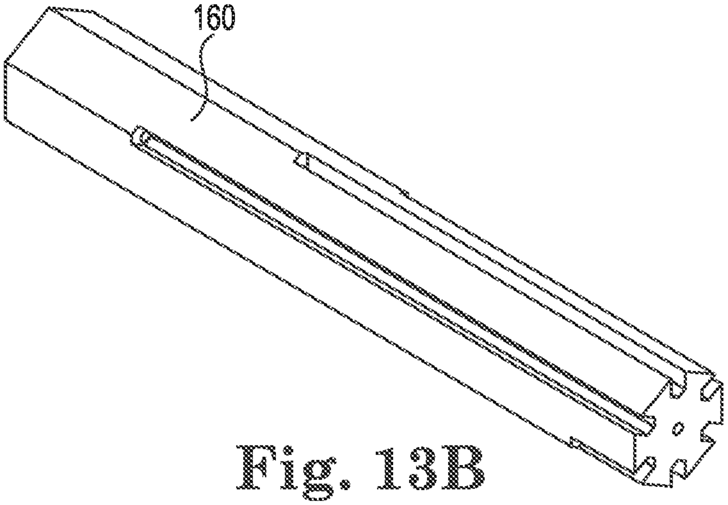

FIGS. 13A and 13B illustrate an assembly frame 160 in accordance with one embodiment. Assembly frame 160 is configured for use similar to that described above relative to assembly frame 60. For example, a plurality of ring-pin subassemblies, such as for example, first-third ring-pin subassemblies 38*a*/48*a*, 38*b*/48*b*, 38*c*/48*c*, can be arranged over assembly frame 160 to form a ring-pin assembly, which can then be overmolded to form a lead connector. Whereas assembly frame 60 illustrated in previous embodiments had a substantially square-shaped outer surface, especially when viewed from its distal end 34 (FIG. 8), assembly frame 160 has an outer surface that is hexagonal. As is evident to one skilled in the art, an assembly frame can have an outer surface with any of a variety of shapes.

Also, whereas assembly frame 60 illustrated in previous embodiments had 3 openings around its perimeter and 3 steps spaced along its length, assembly frame 160 has 6 openings around its perimeter and 6 steps spaced along its length. In this way, assembly frame 160 can accommodate 6 ring-pin subassemblies, ensuring proper spacing between each ring and between each conductor in the ring-pin assemblies. Like assembly frame 60, assembly frame 160 can also be provided with a center opening to accommodate a center pin or other center conductor or the like. As is evident to one skilled in the art, an assembly frame can have any number of steps and openings to accommodate any number of ring-pin subassemblies.

Figure 14:
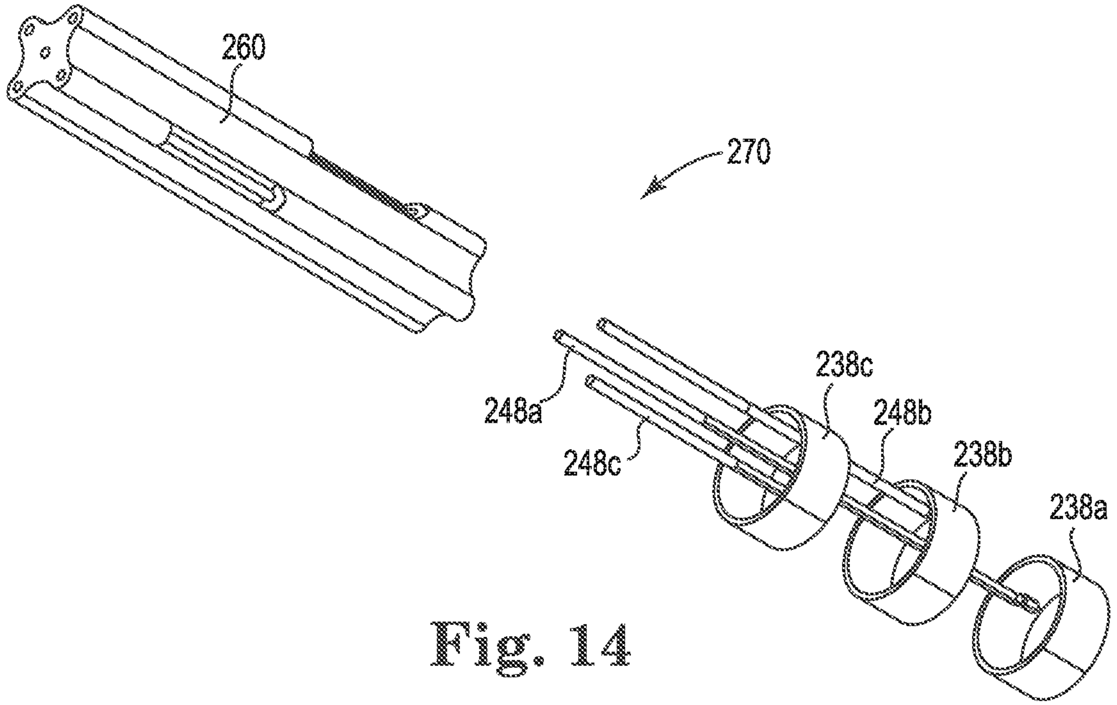
FIG. 14 illustrates an exploded view of a ring-pin assembly, according to one embodiment.

FIG. 14 illustrates an exploded view of a partially assembled ring-pin assembly 270 for forming lead connector 20, where each of first-third ring-pin subassemblies 238*a*/248*a*, 238*b*/248*b*, 238*c*/248*c* are adjacent assembly frame 260. In one embodiment, third ring-pin subassembly 238*c*/248*c* is placed over assembly frame 260 by sliding third conductive pin 248*c* into third opening 268*c* and sliding third ring 238*c* over assembly frame 260 until it engages third step 262*c*. Next, second ring-pin subassembly 238*b*/248*b* is placed over assembly frame 260 by sliding second conductive pin 248*b* into second opening 268*b* and sliding second ring 238*b* over assembly frame 260 until it engages second step 262*b*. Finally, first ring-pin subassembly 238*a*/248*a* is placed over assembly frame 260 by sliding first conductive pin 248*a* into first opening 268*a* and sliding first ring 238*a* over assembly frame 260 until it engages first step 262*a*. In one embodiment, central pin 40 is inserted through fourth opening 268*d* so that it extends out of assembly frame 260 at both its ends. Once fully assembled, the ring-pin assembly is placed in a mold cavity and overmolded into a lead connector as previously described.

Figure 15:
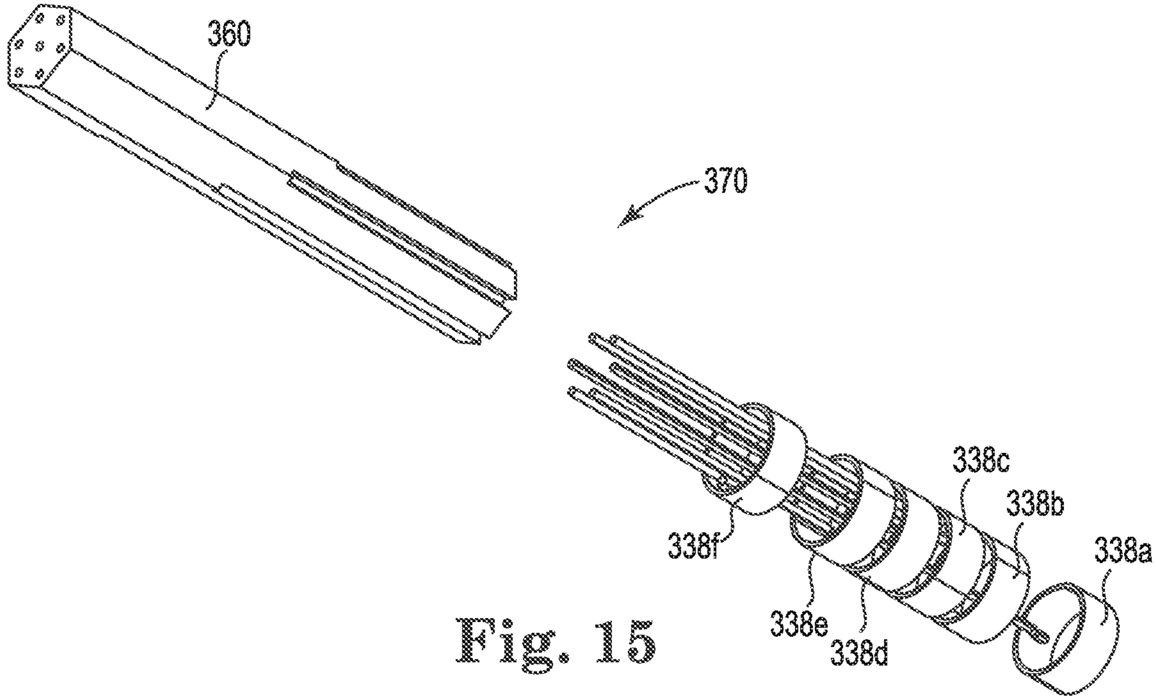
FIG. 15 illustrates an exploded view of a ring-pin assembly, according to one embodiment.

FIG. 15 illustrates an exploded view of a partially assembled ring-pin assembly 370 for forming lead connector 20, where each of first-sixth ring-pin subassemblies 338*a*/348*a*, 338*b*/348*b*, 338*c*/348*c*, 338*d*/348*d*, 338*e*/348*e*, 338*f*/348*f* are adjacent assembly frame 360. In one embodiment, sixth ring-pin subassembly 338*f*/348*f* is placed over assembly frame 360 by sliding sixth conductive pin 348*f* into sixth opening 368*f* and sliding sixth ring 338*f* over assembly frame 360 until it engages sixth step 362*f*Next, fifth ring-pin subassembly 338*b*/348*e* is placed over assembly frame 360 by sliding fifth conductive pin 348*e* into fifth opening 368*e* and sliding fifth ring 338*e* over assembly frame 360 until it engages fifth step 362*e*. Next, fourth ring-pin subassembly 338*d*/348*d* is placed over assembly frame 360 by sliding fourth conductive pin 348*d* into fourth opening 368*d* and sliding fourth ring 338*d* over assembly frame 360 until it engages fourth step 362*d*. Next, third ring-pin subassembly 338*c*/348*c* is placed over assembly frame 360 by sliding third conductive pin 348*c* into third opening 368*c* and sliding third ring 338*c* over assembly frame 360 until it engages third step 362*c*. Next, second ring-pin subassembly 338*b*/348*b* is placed over assembly frame 360 by sliding second conductive pin 348*b* into second opening 368*b* and sliding second ring 338*b* over assembly frame 360 until it engages second step 362*b*. Finally, first ring-pin subassembly 338*a*/348*a* is placed over assembly frame 360 by sliding first conductive pin 348*a* into first opening 368*a* and sliding first ring 338*a* over assembly frame 360 until it engages first step 362*a*.

In one embodiment, central pin 40 is inserted through seventh opening 268*g* so that it extends out of assembly frame 360 at both its ends. Once fully assembled, the ring-pin assembly is placed in a mold cavity and overmolded into a lead connector as previously described.

Figure 16A:
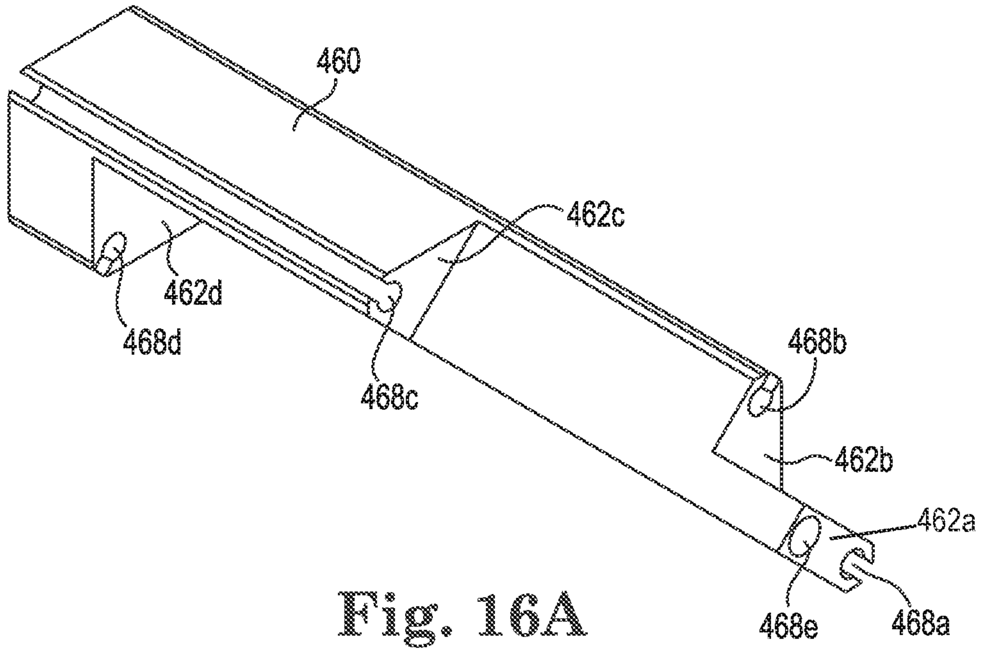
FIGS. 16A-16B illustrate perspective views of an assembly frame, according to one embodiment.
Figure 16B:
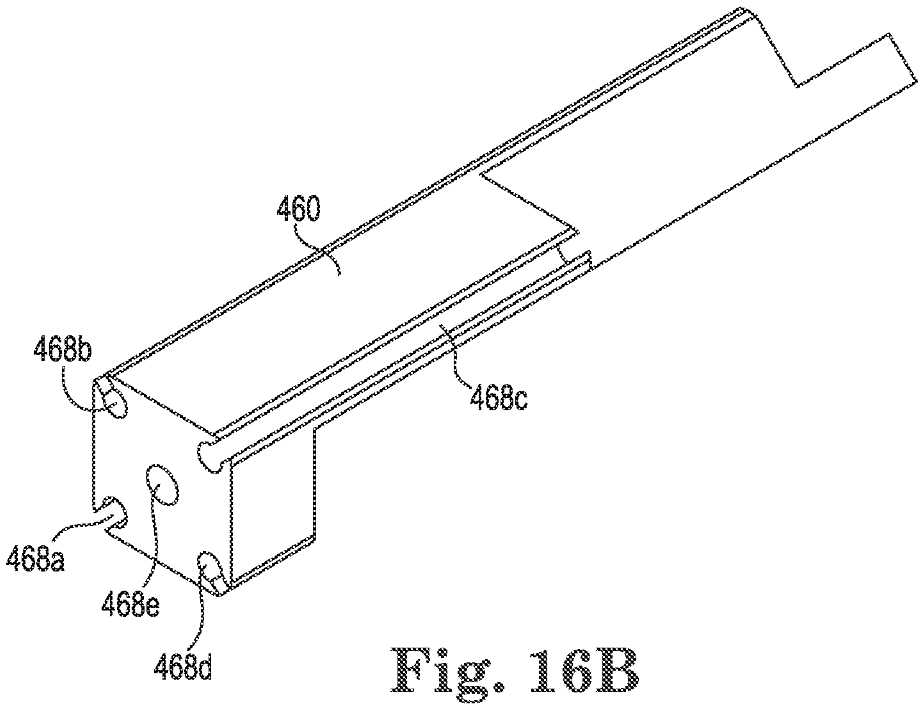

FIGS. 16A-16B illustrate assembly frame 460 in accordance with one embodiment. In one embodiment, assembly frame 460 is configured with first-fourth openings 468*a*, 468*b*, 468*c*, and 468*d* and with first-fourth steps 462*a*, 462*b*, 462*c* and 462*d*. First-fourth steps 462*a*, 462*b*, 462*c* and 462*d* are spaced along the longitudinal dimension of assembly frame 460 such that when a respective ring is placed adjacent the step, the ring will be situated in a desired longitudinal location relative to the final lead connector 20. The longitudinal spaces between steps can be adjusted and tailored to any particular application or standard to ensure proper spacing between rings. First-fourth openings 468*a*, 468*b*, 468*c*, and 468*d* are configured to ensure that respective conductive pins are located properly to ensure conductive contact with appropriate rings and avoid inadvertent contact with the other rings and other conductors. Assembly frame 460 also include fifth opening 468*e* though its center, which can in one embodiment accommodate a central pin.

In the illustrated assembly frame 460, first-fourth openings 468*a*, 468*b*, 468*c*, and 468*d* are configure as slots, with a longitudinally extending narrow slot-opening along the length of each opening. Configuring first-fourth openings 468*a*, 468*b*, 468*c*, and 468*d* as slots can be useful in assembling the pins and may have advantages in tooling in some embodiments. Once assembly frame 460 has respective conductive pins assembled into openings 468*a*, 468*b*, 468*c*, and 468*d* and rings assembled adjacent first-fourth steps 462*a*, 462*b*, 462*c* and 462*d*, it can be overmolded as described above for the other ring-pin assemblies, such that molded material will flow over and into the slots, completely surrounding the conductive pins.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A lead connector for an implantable medical device, the lead connector comprising:

a first and a second ring-pin subassembly each comprising a conductive pin having a proximal end connected to a corresponding ring contact and having a distal end with a pin length defined between the proximal and distal ends;

an assembly frame having a proximal and a distal end and comprising a plurality of openings and a plurality of steps;

wherein a first of the plurality of openings is configured to receive the first ring-pin subassembly such that the conductive pin of the first ring-pin subassembly is inserted into and extends within the first of the plurality of openings such that the length of the conductive pin of the first ring-pin subassembly is contained inside the assembly frame from where it is attached to the corresponding ring contact at its proximal end to its distal end, except where it exits the assembly frame at the distal end, and wherein the corresponding ring contact of the first ring-pin subassembly engages a first of the plurality of steps;

wherein a second of the plurality of openings is configured to receive the second ring-pin subassembly, such that the conductive pin of the second ring-pin subassembly is inserted into and extends within the second of the plurality of openings such that the length of the conductive pin of the second ring-pin subassembly is contained inside the assembly frame from where it is attached to the corresponding ring contact at its proximal end to its distal end, except where it exits the assembly frame at the distal end, and wherein the corresponding ring contact of the second ring-pin subassembly engages a second of the plurality of steps, and an insulating material that at least partially surrounds the corresponding ring contacts and fully surrounds the assembly frame.

2. The lead connector of claim 1, wherein the plurality of openings within the assembly frame are configured to ensure each conductive pin of the conductive pin of the first ring-pin subassembly and the second ring-pin subassembly contacts only one ring contact of the corresponding ring contacts.

3. The lead connector of claim 1, wherein the plurality of openings within the assembly frame are configured to ensure no conductive pin contacts any other conductive pin.

4. The lead connector of claim 1, wherein the plurality of steps are spaced apart along a longitudinal dimension of the assembly frame such that one of the plurality of steps corresponds to the location of one of the corresponding ring contacts of the lead connector.

5. The lead connector of claim 1, wherein the insulating material is the same material as the material of the assembly frame.

6. The lead connector of claim 1, wherein the insulating material is a different material than the material of the assembly frame.

7. The lead connector of claim 1, wherein connecting proximal ends of the conductive pin of the first ring-pin subassembly and the second ring-pin subassembly are coupled to an inner surface of a corresponding ring contact.

8. A ring-pin assembly comprising:

a first and a second ring-pin subassembly each comprising a conductive pin having a proximal end conected to a corresponding ring contact and having a distel end with a pin length defined between the proximal and distal ends;

an assembly frame having a proximal and a distal end and comprising a plurality of openings and a plurality of steps, wherein a first of the plurality of openings is configured to receive the first ring-pin assembly, such that the conductive pin of the first ring-pin assembly is inserted into and extend within the first of the plurality of openings such that length of the conductive pin of the first ring-pin subassembly is contained inside the assembly frame from where it is attached to the corresponding ring contact at its proximal end to its distal end, except where it exits the assembly frame at the distal end, and wherein the corresponding ring contact of the first ring-pin subassembly engage a first of the plurality of steps;

wherein a second of the plurality of openings is configured to receive the second ring-pin subassembly such that the conductive pin of the second ring-pin subassembly is inserted into the extends with the second of the plurality of openings such that the length of the conductive pin of the second ring-pin subassembly is contained inside the assembly frame from where it is attached to the corresponding ring contact at its proximal end to its distal end, except where it exits the assembly fram at the distal end, and wherein the corresponding ring contact of the second ring-pin subassembly engages a second of the plurality of steps.

9. The ring-pin assembly of claim 8, wherein an insulating material at least partially surrounds the corresponding ring contacts and fully surrounds the assembly frame, thereby forming a lead connector.

* * * * *